(12) United States Patent
Zhong

(10) Patent No.: US 9,282,744 B2
(45) Date of Patent: Mar. 15, 2016

(54) SYNERGISTIC FUNGICIDE COMPOSITION

(75) Inventor: Hangen Zhong, Dafeng (CN)

(73) Assignee: JIANGSU HUIFENG AGROCHEMICAL CO., LTD., Dafeng (CN)

( * ) Notice: Subject to any disclaimer, the term of this patent is extended or adjusted under 35 U.S.C. 154(b) by 0 days.

(21) Appl. No.: 14/421,125

(22) PCT Filed: Aug. 20, 2012

(86) PCT No.: PCT/CN2012/080379
§ 371 (c)(1),
(2), (4) Date: Feb. 11, 2015

(87) PCT Pub. No.: WO2014/026396
PCT Pub. Date: Feb. 20, 2014

(65) Prior Publication Data
US 2015/0208659 A1 Jul. 30, 2015

(30) Foreign Application Priority Data

Aug. 13, 2012 (CN) .......................... 2012 1 0287687

(51) Int. Cl.
| | |
|---|---|
| *A01N 47/38* | (2006.01) |
| *A01N 43/653* | (2006.01) |
| *A01N 43/84* | (2006.01) |
| *A01N 43/80* | (2006.01) |
| *A01N 43/32* | (2006.01) |

(52) U.S. Cl.
CPC ................ *A01N 47/38* (2013.01); *A01N 43/32* (2013.01); *A01N 43/653* (2013.01); *A01N 43/80* (2013.01); *A01N 43/84* (2013.01)

(58) Field of Classification Search
CPC ....... A01N 47/38; A01N 43/80; A01N 43/32; A01N 43/84; A01N 43/653
USPC ...................................... 514/237.5
See application file for complete search history.

(56) References Cited

PUBLICATIONS

Translation of abstract of CN 101796955 A (Mingrui Wang, Aug. 11, 2010).*

* cited by examiner

*Primary Examiner* — Kristin Vajda
(74) *Attorney, Agent, or Firm* — CBM Patent Consulting, LLC

(57) ABSTRACT

A synergistic fungicide composition, a formulation method and a use thereof are provided. The composition contains two active components A and B, where the active component A is benziothiazolinone, the active component B is one selected from dithianon, dimethomorph, iprodione and epoxiconazol, and the weight ratio of the two components is 1:50 to 50:1, and preferably 1:30 to 30:1. Test results show that, the fungicide composition has a significant synergistic effect, and more importantly, the application amount and the use-cost are reduced. The fungicide composition is effective in preventing and treating certain fungal diseases of crops such as food crops, vegetables and fruits.

8 Claims, No Drawings

SYNERGISTIC FUNGICIDE COMPOSITION

This application is the U.S. national phase of International Application No. PCT/CN2012/080379 Filed on 20 Aug. 2012. which designated the U.S. and claims priority to Chinese Application No. 201210287687.2 filed on 13 Aug. 2012, the entire contents of each of which are hereby incorporated by reference.

BACKGROUND

1. Technical Field

The present invention belongs to the field of agricultural plant protection, particularly to a fungicide composition with improved performance, and specifically relates to a fungicide composition containing two active components.

2. Related Art

Benziothiazolinone is a fungicide and has the following functions and features: being a novel broad-spectrum fungicide, and being effective in preventing and treating fungal diseases. In the fungicidal process, the nucleus structure of the pathogenic fungi is destroyed, resulting lost of the heat part and death due to failure, the metabolism of the pathogenic fungus cells was interfered, resulting in physiologic disorders, and finally, leading to death. The pathogenic fungi are completely killed, and the desired effect of eradicating pathogenic fungi is achieved. Benziothiazolinone is mainly used in preventing and treating cucumber downy mildew, pear scab, apple scab, orange anthracnose, grape anthracnose, and is effective in preventing and treating various bacterial diseases and fungal diseases.

Dimethomorph is a morpholine-based broad-spectrum fungicide, has a unique mode of action on fungi of Peronosporales and Peronophthoraceae of phycomycetes, and is mainly to cause degradation of sporangium wall, so as to cause death of fungi. Dimethomorph is fungicide dedicated to oomycetes fungi, and has the functions and features of destroying the formation of cell membrane, having effects in all stages of life cycle of oomycetes, being particularly sensitive in the formation stages of sporangiophores and oospores, being inhibited at a very low concentration (0.25 μg/ml), and having no cross resistance with phenylamides reagents.

Dithianon is a protective fungicide used for various leaf diseases of many pomefruits and stone fruits, has multi-mechanism. By reacting with a sulfur-containing groups and interfering with cell respiration, dithianon inhibits a series of fungal enzymes, and finally causes death of fungi. Dithianon has good protective activity and a certain therapeutic activity. Suitable fruit crops include pomefruits and stone fruits such as apple, pear, peach, apricots, cherry, citrus, coffee, grape, strawberry and hop. Except powdery mildew, objects of prevention and treatment include almost all fruit tree diseases such as scab, mildew disease, leaf spot, rust, anthracnose, scab, downy mildew and brown rot.

Iprodione is a high-efficient dicarbonylimides broad-spectrum contact-type fungicide, has a certain treatment and prevention effect, and can be absorbed through roots and exert the systemic action. Iprodione is effective in preventing and treating fungi resistant to benzimidazoles absorption-type fungicides, and is suitable in preventing and treating diseases such as early leaf disease, gray mold and early blight of various fruit trees, vegetables, fruits and other crops.

Epoxiconazol is an absorption-type triazoles fungicide, has the mechanism of action of inhibiting synthesis of ergosterol pathogenic fungus and hindering the formation of the cell wall of pathogenic fungi. Epoxiconazol not only has good protecting, treating and eradicating activity, but also has absorption and good residual activity. Epoxiconazol can improve the chitinase activity of crops, thereby causing shrink of fungal haustoria, and inhibiting the invasion of pathogenic fungi, which is the unique characteristic of epoxiconazol among all triazoles products. Epoxiconazol has a good prevention and treatment effect on diseases such as leaf spot, powdery mildew and rust of crops such as bananas, garlic, celery, beans, melons, asparagus, peanuts and sugar beet and anthracnose, white rot of grapes.

Actual experiences of fungicide have shown that repeat application of one specific active compound to prevent and treat fungi will results in quick selectivity of fungal strains in many cases, in order to lower risk of selectivity of fungal strains, a mixture of compounds of different activities are commonly used to prevent and treat harmful fungi presently. Active compounds having different mechanisms of action are combined to delay the generation of resistance, and reduce the application amount and prevention and treatment costs.

SUMMARY

In view of the problems of fungicide resistance and residual in soil in practical applications, the technical problem to be solved by the present invention is: screening two fungicides of different fungicidal principles for combination, to improve the prevention and treatment effect of the fungicide, delay the emergence of resistance, reduce the application amount and prevention and treatment costs.

In order to solve the above technical problems, the present invention provides a fungicide composition. The composition contains two active components A and B, the active component A is benziothiazolinone, and the active component B is one selected from dithianon, dimethomorph, iprodione and epoxiconazol. The inventers find from experiments that the fungicide composition has a significant synergistic effect, and more importantly, the application amount and the use-cost are reduced. Compounds containing the component A and the component B have different structures, different mechanisms of action, the fungicidal spectrum can be expanded by combination of the two components, and the emergence and development speed of resistance of the pathogenic fungi is delayed, and moreover, the component A and the component B have no cross resistance.

Another objective of the present invention is to provide a method for preparing a fungicide composition containing two active components A and B and a use of the fungicide composition containing two active components A and B in the preventing and treating food crop diseases in the field of agriculture.

In the fungicide composition, the weight ratio of the component A and the component B is 1:50 to 50:1, and preferably 1:30 to 30:1.

The fungicide composition of the present invention is composed of 6 wt % to 92 wt % of active components and 94 wt % to 8 wt % of fungicide adjuvants.

The present invention provides a use of a fungicide composition containing a component A (benziothiazolinone) and a component B (one selected from dithianon, dimethomorph, iprodione and epoxiconazol) in preventing and treating plant diseases.

The composition further contains a support, an adjuvant and/or a surfactant. During application, a common adjuvant can be mixed with the composition.

Suitable adjuvants may be a solid or liquid, and are generally a substance commonly used in formulation processing process, for example, natural or regenerated minerals, solvents, dispersing agents, wetting agents, adhesives, thickeners, binders or fertilizers.

A method for applying the composition of the present invention includes: applying the composition of the present invention on the aboveground part of plants, especially the leaves or foliages. The frequency of application and application amount depend on the biological characteristics and the climate survival conditions of the pathogen. A liquid formulation containing the composition may be used to wet the plant growing place such as rice field, or the composition may be applied in the soil in the solid form, such as in the granular form (soil application), so that the composition can get into the plant body (systemic action) through the plant roots from the soil.

These compositions may merely contain the active components and be applied, and may also mixed with additives for use, so the composition of the present invention may be formulated into various formulations, for example, wettable powder, a suspension, an oil suspension, a water dispersible granule, an emulsion in water and a microemulsion. According to the properties of these compositions and the purpose to be achieved by applying the composition as well as the environmental conditions, the method for applying the composition may be selected to be spraying, atomizing, dusting, scattering or pouring and the like.

The composition of the present invention can be formulated into various formulations by known methods, the active components and an adjuvant such as a solvent and a solid support may be fully mixed with a surfactant and granulated when required, and formulated into a desired formulation.

The solvent may be selected from: aromatic hydrocarbons, and preferably aromatic hydrocarbons containing 8 to 12 carbon atoms, for example, xylene mixture or substituted benzene; phthalates, for example, dibutyl phthalates and dioctyl phthalate; aliphatic hydrocarbons, for example, cyclohexane and paraffins; alcohols and glycols and ethers and esters thereof, for example, ethanol, ethylene glycol, ethylene glycol monomethyl; ketones, for example, cyclohexanone; strongly polar solvent, for example, N-methyl-2-pyrrolidone, dimethyl sulfoxide and dimethylformamide; and vegetable oils, for example, soybean oil.

The solid supports useful in powder and dispersible granule are generally natural mineral fillers, for example, talc, kaolin, montmorillonite and attapulgite. For the control of the physical performance of the composition, highly dispersed silicic acid or a highly dispersed adsorbing polymer support such as a granular adsorbing support and non-adsorbing support may be added, where a suitable granular adsorbing support is porous, for example, pumice, bentonite and bentonite; a suitable non-adsorbing support is, for example, calcite and sand. Furthermore, a large amount of inorganic or organic preformed granular materials, especially, dolomite, may be used as support.

According to the chemical properties of the active components in the composition of the present invention, a suitable surfactant is lignosulfonic acid, naphthalenesulfonic acid, phenolsulfonic acid, alkaline earth metal or ammonium salts, alkylaryl sulfonates, alkyl sulfates, alkyl sulfonates, fatty alcohol sulphates and fatty acids and sulfated fatty alcohol ethylene glycol esters, condensates of sulfonated naphthalene and naphthalene derivatives with formaldehyde, condensates of naphthalene or naphthalenesulfonic acid with phenol and formaldehyde, polyoxyethylene octyl phenyl ether, ethoxylated iso-octyl phenol, octyl phenol, nonylphenol, alkylaryl polyglycol ethers, triutylbenzene polyglycol ethers, tristearylphenyl polyglycol ethers, alkylaryl polyether alcohols, ethoxylated caster oil, polyoxyethylene alkyl ethers, ethylene oxide condensates, ethoxylated polyoxypropylene, lauric acid polyethylene glycol ether acetal, sorbate, lignosulphite wasterwater and methylcellulose.

The two active components in the composition of the present invention has a synergistic effect, and the activity of the composition is more significant than the sum of the expected activity of using single compounds and the individual activity of single compounds. Due to the synergistic effect, the application amount is decreased, and the fungicidal control spectrum is broadened, the prevention and treatment effects can be achieved quickly and last longer, so that by merely one or several times of application, the fungi harmful to plants can be controlled better, and the possible application interval is widened. There features are specially required in the practice process of controlling plant fungi. The composition of the present invention is especially effective for the following food crop diseases: cucumber downy mildew pathogenic fungi, cucumber gray mold, sigatoka, grape downy mildew and litchi blight.

The fungicide composition of the present invention also has other features: 1. the mixture of composition of the present invention has a significant synergistic effect; 2, since the two single components of the composition have great difference in structure, and completely different mechanisms of action, and have no cross resistance, the resistance generated when the two single components are used alone can be delayed; 3. the composition of the present invention is safe to crops and has a good prevention and treatment effect. It is proved by test that, the fungicide composition of the present invention has stable chemical properties and significant synergistic effect, and exhibits a significant synergistic effect and complementary effect on prevention and treatment targets.

BRIEF DESCRIPTION OF THE DRAWINGS

No drawings.

DETAILED DESCRIPTION

In order to make the objective, technical solutions and advantages of the present invention clearer and more comprehensive, the present invention is further described in detail below with the following embodiments. It should be understood that, the specific embodiment described herein are merely used to illustrate the present invention, but are not intended to limit the present invention, and any modification, equivalent replacement and improvement made within the spirit and principle of the present invention shall all fall within the protection scope of the present invention.

Percentages in all formulas in the following embodiments all are weight percentages. Processes for processing the preparations of the composition of the present invention all are existing technologies, and may vary according to different conditions.

I) Embodiments of Preparation of Formulations (I) Processing of Water Dispersible Granule and Embodiments The active component benziothiazolinone and one of dithianon, dimethomorph, iprodione and epoxiconazol were fully mixed with an adjuvant and a filler at the formula ratio, the mixture was pulverized into wettable powder by airflow, and the wettable powder was mixed with a certain amount of water and then subjected to extrusion granulation, drying and sieving, to obtain the water dispersible granule product.

Embodiment 1

62% Benziothiazolinone.Dithianon Water Dispersible Granule

60% benziothiazolinone, 2% dithianon, 4% sodium alkyl naphthalene sulfonate, 3% sodium dodecyl sulfonate, 3% ammonium sulfate, complemented to 100% with light calcium carbonate.

Embodiment 2

65% Benziothiazolinone.Dithianon Water Dispersible Granule

2% benziothiazolinone, 63% dithianon, 5% sodium lignosulfonate, 7% sodium methyl naphthalene sulfonate-formaldehyde condensate, 3% sodium dodecyl sulfate, complemented to 100% with diatomite.

Embodiment 3

65% Benziothiazolinone.Dimethomorph Water Dispersible Granule

63% benziothiazolinone, 2% dimethomorph, 6% sodium lignosulfonate, 3% sodium dodecyl sulfonate, 1% xanthan gum, 1% sodium carboxymethyl starch, complemented to 100% with attapulgite.

Embodiment 4

85% Benziothiazolinone.Dimethomorph Water Dispersible Granule

2% benziothiazolinone, 83% dimethomorph, 1% ammonium sulfate, 2% alginate, 1% sodium methyl naphthalene sulfonate-formaldehyde condensate, 1% organosilicone, complemented to 100% with bentonite.

Embodiment 5

62% Benziothiazolinone.Iprodione Water Dispersible Granule

60% benziothiazolinone, 2% iprodione, 2% sodium dodecyl sulfonate, 2% sodium alkyl naphthalene sulfonate, 3% ammonium sulfate, complemented to 100% with light calcium carbonate.

Embodiment 6

75% Benziothiazolinone.Iprodione Water Dispersible Granule

2% benziothiazolinone, 73% iprodione, 5% sodium methyl naphthalene sulfonate-formaldehyde condensate, 4% sodium lignosulfonate, 3% sodium dodecyl sulfate, complemented to 100% with diatomite.

Embodiment 7

62% Benziothiazolinone.Epoxiconazol Water Dispersible Granule

60% benziothiazolinone, 2% epoxiconazol, 1% sodium carboxymethyl starch, 4% sodium dodecyl sulfonate, 4% sodium lignosulfonate, 1% xanthan gum, complemented to 100% with attapulgite.

Embodiment 8

62% Benziothiazolinone.Epoxiconazol Water Dispersible Granule

2% benziothiazolinone, 60% epoxiconazol, 1% ammonium sulfate, 2% alginate, 1% sodium methyl naphthalene sulfonate-formaldehyde condensate, 1% organosilicone, complemented to 100% with bentonite.

(II) Processing of Suspension and Embodiments

The active component benziothiazolinone and one of dithianon, dimethomorph, iprodione and epoxiconazol were fully mixed with the components such as a dispersant, a wetting agent, a thickener and water at the formula ratio, the mixture was then subjected to sanding and/or high-speed shearing, to obtain a semi-finished product, and the semi-finished product was fully mixed water after analysis and filtered, to obtain the finished product.

Embodiment 9

35% Benziothiazolinone.Dithianon Suspension

25% benziothiazolinone, 100% dithianon, 7% sodium lignosulfonate, 0.8% xanthan gum, 3% bentonite, 1% magnesium aluminum silicate, 4% ethylene glycol, complemented to 100% with water.

Embodiment 10

36% Benziothiazolinone.Dithianon Suspension

12% benziothiazolinone, 24% dithianon, 6% sodium methyl naphthalene sulfonate-formaldehyde condensate, 4% bentonite, 5% glycerol, complemented to 100% with water.

Embodiment 11

42% Benziothiazolinone.Dimethomorph Suspension

40% benziothiazolinone, 2% dimethomorph, 7% polyoxyethylene fatty alcohol ether phosphate, 3% white carbon black, 6% glycerol, 2% calcium benzoate, complemented to 100% with water.

Embodiment 12

32% Benziothiazolinone.Dimethomorph Suspension

5% benziothiazolinone, 27% dimethomorph, 7% sodium lignosulfonate, 3% white carbon black, 6% ethylene glycol, 1% xanthan gum, complemented to 100% with water.

Embodiment 13

55% Benziothiazolinone.Iprodione Suspension

50% benziothiazolinone, 5% iprodione, 7% polyoxyethylene fatty alcohol ether phosphate, 3% white carbon black, 6% glycerol, 2% calcium benzoate, complemented to 100% with water.

Embodiment 14

42% Benziothiazolinone.Iprodione Suspension

2% benziothiazolinone, 40% iprodione, 7% sodium lignosulfonate, 3% white carbon black, 6% ethylene glycol, 1% xanthan gum, complemented to 100% with water.

Embodiment 15

55% Benziothiazolinone.Epoxiconazol Suspension

50% benziothiazolinone, 5% epoxiconazol, 7% polyoxyethylene fatty alcohol ether phosphate, 3% white carbon black, 6% glycerol, 2% calcium benzoate, complemented to 100% with water.

Embodiment 16

55% Benziothiazolinone.Epoxiconazol Suspension

5% benziothiazolinone, 50% epoxiconazol, 7% sodium lignosulfonate, 3% white carbon black, 6% ethylene glycol, 1% xanthan gum, complemented to 100% with water.

(III) Processing of Wettable Powder and Embodiments

The active component A benziothiazolinone and the active component B of one of dithianon, dimethomorph, iprodione and epoxiconazol were fully mixed with various adjuvants and fillers at ratios, and the mixture was pulverized by an ultrafine pulverizer, to obtain a wettable powder.

Embodiment 17

90% Benziothiazolinone.Dithianon Wettable Powder

2% benziothiazolinone, 88% dithianon, 2% calcium lignosulphonate, 1% sodium dodecylbenzene sulfonate, 2% bentonite, complemented to 100% with attapulgite.

Embodiment 18

88% Benziothiazolinone.Dithianon Wettable Powder

86% benziothiazolinone, 2% dithianon, 1% polyoxyethylene alkyl ether sulfonate, 2% nekal, 1.5% bentonite, 2% white carbon black, complemented to 100% with diatomite 100%.

Embodiment 19

55% Benziothiazolinone.Dithianon Wettable Powder

25% benziothiazolinone, dithianon 30%, 6% alkyl sulfonate, 6% sodium lignosulfonate, 11% white carbon black, complemented to 100% with kaolin.

Embodiment 20

88% Benziothiazolinone.Dimethomorph Wettable Powder

86% benziothiazolinone, 2% dimethomorph, 2% polyoxyethylene octyl phenyl ether, 6% sodium lignosulfonate, 4% white carbon black, complemented to 100% with diatomite.

Embodiment 21

50% Benziothiazolinone.Dimethomorph Wettable Powder

25% benziothiazolinone, 25% dimethomorph, 7% calcium lignosulphonate, 5% white carbon black, 3% sodium dodecylbenzene sulfonate, complemented to 100% with attapulgite.

Embodiment 22

62% Benziothiazolinone.Dimethomorph Wettable Powder

2% benziothiazolinone, 60% dimethomorph, 5% calcium lignosulphonate, 4% bentonite, 3% polyoxyethylene octyl phenyl ether, complemented to 100% with attapulgite.

Embodiment 23

85% Benziothiazolinone.Iprodione Wettable Powder

83% benziothiazolinone, 2% iprodione, 1% polyoxyethylene octyl phenyl ether, 2% sodium lignosulfonate, 3% white carbon black, complemented to 100% with diatomite.

Embodiment 24

50% Benziothiazolinone.Iprodione Wettable Powder

25% benziothiazolinone, 25% iprodione, 3% sodium dodecylbenzene sulfonate, 5% white carbon black, 7% calcium lignosulphonate, complemented to 100% with attapulgite.

Embodiment 25

85% Benziothiazolinone.Iprodione Wettable Powder

3% benziothiazolinone, 82% iprodione, 5% calcium lignosulphonate, 4% bentonite, 3% polyoxyethylene octyl phenyl ether, complemented to 100% with attapulgite.

Embodiment 26

88% Benziothiazolinone.Epoxiconazol Wettable Powder

2% benziothiazolinone, 86% epoxiconazol, 2% sodium dodecylbenzene sulfonate, 1% bentonite, 2% calcium lignosulphonate, complemented to 100% with attapulgite.

Embodiment 27

86% Benziothiazolinone.Epoxiconazol Wettable Powder

84% benziothiazolinone, 2% epoxiconazol, 1% nekal, 2% polyoxyethylene alkyl ether sulfonate, 15% bentonite, 2% white carbon black, complemented to 100% with diatomite 100%.

Embodiment 28

50% Benziothiazolinone.Epoxiconazol Wettable Powder

25% benziothiazolinone, 25% epoxiconazol, 6% sodium lignosulfonate, 6% alkyl sulfonate, 11% white carbon black, complemented to 100% with kaolin.

(IV) Processing of Microemulsion and Embodiments

The active component A benziothiazolinone and the active component B of one of dithianon, dimethomorph, iprodione and epoxiconazol were completely dissolved in a solvent, and at the same time, an emulsifier, a synergistic effect adjuvant and a cryoprotectant were added with stirring, after the system was fully mixed, water was slowly added to the mixture, and the mixture was fully stirred, to obtain a microemulsion of different contents.

Embodiment 29

18% Benziothiazolinone.Dithianon Microemulsion

3% benziothiazolinone, 15% dithianon, 15% acetone, 0.5% compound sodium nitrophenolate, 5% alkyl polyoxyethylene ether and nonylphenol polyoxyethylene ether, 1% propylene glycol, 2% urea, complemented to 100% with water.

Embodiment 30

30% Benziothiazolinone.Dithianon Microemulsion

25% benziothiazolinone, 5% dithianon, 4% polyoxyethylene aliphatate and phenethyl phenol polyoxyethylene ether, 2% glycerol, 11% methanol, 1% azone, complemented to 100% with water.

Embodiment 31

15% Benziothiazolinone.Dimethomorph Microemulsion

5% benziothiazolinone, 10% dimethomorph, 16% alkyl benzene sulfonate and alkyl naphthalene sulfonate, 1% thiazone, 16% ethyl acetate, 1% propylene glycol, complemented to 100% with water.

Embodiment 32

15% Benziothiazolinone.Dimethomorph Microemulsion

10% benziothiazolinone, 5% dimethomorph, 8% calcium dodecylbenzene sulfonate, 0.5% thiazone, 14% sorbic acid, 3% polyethylene glycol, complemented to 100% with water.

Embodiment 33

18% Benziothiazolinone.Iprodione Microemulsion

6% benziothiazolinone, 12% iprodione, 15% acetone, 0.5% compound sodium nitrophenolate, 5% alkyl polyoxyethylene ether and nonylphenol polyoxyethylene ether, 1% propylene glycol, 2% urea, complemented to 100% with water.

Embodiment 34

21% Benziothiazolinone.Iprodione Microemulsion

20% benziothiazolinone, 1% iprodione, 4% polyoxyethylene aliphatate and phenethyl phenol polyoxyethylene ether, 2% glycerol, 11% methanol, 1% azone, complemented to 100% with water.

Embodiment 35

12% Benziothiazolinone.Epoxiconazol Microemulsion

2% benziothiazolinone, 10% epoxiconazol, 1% propylene glycol, 13% alkyl benzene sulfonate and alkyl naphthalene sulfonate, 1% thiazone, 11% ethyl acetate, complemented to 100% with water.

Embodiment 36

15% Benziothiazolinone.Epoxiconazol Microemulsion

10% benziothiazolinone, 5% epoxiconazol, 14% sorbic acid, 1% thiazone, 7% calcium dodecylbenzene sulfonate, 2% polyethylene glycol, complemented to 100% with water.

(V) Processing of Emulsion in Water and Embodiments

In an emulsifying kettle, the active component A benziothiazolinone and the active component B of one of dithianon, dimethomorph, iprodione and epoxiconazol were fully mixed with a solvent and an adjuvant under mechanical stirring, an emulsifier and a stabilizer were then added and fully stirred, finally, water was added, and the mixture was stirred for 10 to 30 min at a rotation rate of 100 to 12000 rpm, to obtain a uniform emulsion product.

Embodiment 37

42% Benziothiazolinone.Dithianon Emulsion in Water

40% benziothiazolinone, 2% dithianon, 4% dimethyl N-phthalate, 3% nonylphenol phenoxy vinyl ether, 2% 2,6-tert-butyl-4-methylphenol, 3% ethylene glycol, 1% polyvinyl alcohol, 1% calcium benzoate, 0.8% organic silicon defoamer, complemented to 100% with water.

Embodiment 38

44% Benziothiazolinone.Dithianon Emulsion in Water

4% benziothiazolinone, 40% dithianon, 4% butylhydroxyanisole, 3% plyisobutylene anhydride-polyethylene glycol copolymer, 2% propylene glycol, 3% xanthan gum, 1% polyvinyl alcohol, 1.2% organic silicon defoamer, complemented to 100% with water.

Embodiment 39

22% Benziothiazolinone.Dimethomorph Emulsion in Water

20% benziothiazolinone, 2% dimethomorph, 3% polyoxyethylene block copolymer, 1% propylene glycol, 2% xanthan gum, 3% plyisobutylene anhydride-polyethylene glycol copolymer, 1.2% organic silicon defoamer, complemented to 100% with water.

Embodiment 40

22% Benziothiazolinone.Dimethomorph Emulsion in Water

2% benziothiazolinone, 20% dimethomorph, 2% N-dodecylpyrrolidone, 1% polyoxyethylene castor oil, 3% glycerol, 12% polyvinyl alcohol, 1% calcium benzoate, 2% isooctanol, complemented to 100% with water.

Embodiment 41

30% Benziothiazolinone.Iprodione Emulsion in Water

25% benziothiazolinone, 5% iprodione, 1% 2,6-tert-butyl-4-methylphenol, 2% nonylphenol phenoxy vinyl ether, 3% ethylene glycol, 1% calcium benzoate, 2% dimethyl N-phthalate, 1% polyvinyl alcohol, 1% organic silicon defoamer, complemented to 100% with water.

Embodiment 42

42% Benziothiazolinone.Iprodione Emulsion in Water

2% benziothiazolinone, 40% iprodione, 2% propylene glycol, 3% butylhydroxyanisole, 3% plyisobutylene anhydride-polyethylene glycol copolymer, 3% xanthan gum, 1% polyvinyl alcohol, 1.2% organic silicon defoamer, complemented to 100% with water.

Embodiment 43

21% Benziothiazolinone.Epoxiconazol Emulsion in Water

20% benziothiazolinone, 1% epoxiconazol, 1% propylene glycol, 1% xanthan gum, 2% plyisobutylene anhydride-polyethylene glycol copolymer, 2% polyoxyethylene block copolymer, 1.5% organic silicon defoamer, complemented to 100% with water.

Embodiment 44

42% Benziothiazolinone.Epoxiconazol Emulsion in Water

2% benziothiazolinone, 40% epoxiconazol, 2% polyoxyethylene castor oil, 1% N-dodecylpyrrolidone, 2% glycerol, 1.1% polyvinyl alcohol, 2% calcium benzoate, 1% isooctanol, complemented to 100% with water.

(VI) Processing of Oil Suspension and Embodiments

The active component A benziothiazolinone and the active component B of one of dithianon, dimethomorph, iprodione and epoxiconazol were mixed with various components such as a dispersant, a stabilizer, a defoamer and a solvent at the formula ratio, and the mixture was placed in a sanding kettle for milling, then sent to a homogenizer and fully mixed, to obtain the finished product.

Embodiment 45

42% Benziothiazolinone.Dithianon Oil Suspension

2% benziothiazolinone, 40% dithianon, 8% sodium lignosulfonate, 4% bentonite, 1% xanthan gum, 2% organic silicon defoamer, complemented to 100% with soybean oil.

Embodiment 46

55% Benziothiazolinone.Dithianon Oil Suspension

50% benziothiazolinone, 5% dithianon, 8% nekal, 5% bentonite, 2% organosilicone, complemented to 100% with engine oil.

Embodiment 47

30% Benziothiazolinone.Dimethomorph Oil Suspension

25% benziothiazolinone, 5% dimethomorph, 8% naphthalene sulfonic acid-formaldehyde condensate, 5% diatomite, 2% aluminium-magnesium silicate, complemented to 100% with dichloroethane.

Embodiment 48

42% Benziothiazolinone.Dimethomorph Oil Suspension

2% benziothiazolinone, 40% dimethomorph, 11% sodium lignosulfonate, 4% aerosil, 2% aluminium-magnesium silicate, complemented to 100% with castor oil.

Embodiment 49

18% Benziothiazolinone.Iprodione Oil Suspension

3% benziothiazolinone, 15% iprodione, 1% organic silicon defoamer, 3% bentonite, 7% sodium lignosulfonate, 1% xanthan gum, complemented to 100% with soybean oil.

Embodiment 50

22% Benziothiazolinone.Iprodione Oil Suspension

20% benziothiazolinone, 2% iprodione, 3% bentonite, 7% nekal, 2% organosilicone, complemented to 100% with engine oil.

Embodiment 51

30% Benziothiazolinone.Epoxiconazol Oil Suspension

25% benziothiazolinone, 5% epoxiconazol, 8% naphthalene sulfonic acid-formaldehyde condensate, 5% diatomite, 2% aluminium-magnesium silicate, complemented to 100% with dichloroethane.

Embodiment 52

45% Benziothiazolinone.Epoxiconazol Oil Suspension

15% benziothiazolinone, 30% epoxiconazol, 11% sodium lignosulfonate, 4% aerosil, 2% aluminium-magnesium silicate, complemented to 100% with castor oil.

II) Efficacy Verification Test

(I) Biological Assay Embodiments

1. Test of Toxicity of Compound Benziothiazolinone and Dithianon on Cucumber Downy Mildew Pathogenic Fungi Subjects for Test: Cucumber Downy Mildew Pathogenic Fungi The incidence of whole cucumber leaves was investigated according to test grading level, and the disease index and the prevention and treatment effect were calculated.

The prevention and treatment effect was converted into probability values (y), the heights of the chemicals (μg/ml) were converted into logarithm values (x), the toxicity equation and the median inhibition concentration EC50 were calculated by the least square method, and the toxicity index level co-toxicity coefficient (CTC) of the chemicals was calculated according to the Sun Yunpei's method.

Actual toxicity index(ATI)=(EC50 of the standard reagent/EC50 of the test reagent)×100

Theoretical toxicity index(TTI)=the toxicity index of chemical $A$×the percentage of $A$ in the mixture+ the toxicity index of chemical $B$×the percentage of $B$ in the mixture Co-toxicity coefficient(CTC)=[Actual toxicity index (ATI) of the mixture/Theoretical toxicity index (TTI) of the mixture]×00

CTC≤80, indicating that the composition had the antagonistic effect, 80<CTC<120, indicating that the composition had the additive effect, and CTC≥20, indicating that the composition had the synergistic effect.

TABLE 1

Analysis of results of test of toxicity of benziothiazolinone, dithianon and compound benziothiazolinone and dithianon on cucumber downy mildew

| Names of reagents | EC$_{50}$ (μg/ml) | ATI | TTI | Co-toxicity coefficient (CTC) |
|---|---|---|---|---|
| Benziothiazolinone | 3.25 | 100.0 | / | / |
| Dithianon | 5.41 | 60.1 | / | / |
| Benziothiazolinone:dithianon ratio = 50:1 | 2.37 | 137.13 | 99.215 | 138.215 |
| Benziothiazolinone:dithianon ratio = 30:1 | 1.91 | 170.16 | 98.67 | 172.454 |
| Benziothiazolinone:dithianon ratio = 10:1 | 1.58 | 205.69 | 96.37 | 213.438 |
| Benziothiazolinone:dithianon ratio = 1:1 | 2.08 | 156.25 | 80.05 | 195.191 |
| Benziothiazolinone:dithianon ratio = 1:10 | 2.26 | 143.81 | 63.73 | 225.655 |
| Benziothiazolinone:dithianon ratio = 1:30 | 3.79 | 85.61 | 61.43 | 139.358 |
| Benziothiazolinone:dithianon ratio = 1:50 | 4.18 | 77.76 | 60.88 | 127.720 |

The results (Table 1) show that, the compound benziothiazolinone and dithianon has significantly improved prevention and treatment effect on cucumber downy mildew, indicating that the compound of the two has a significant synergistic effect on cucumber downy mildew pathogenic fungi. Especially when the ratio of benziothiazolinone and dithianon is in the range of 1:30 to 30:1, the co-toxicity coefficient of benziothiazolinone and dithianon is 135 and more, and the synergistic effect is significant.

2. Test of Toxicity of Compound Benziothiazolinone and Dimethomorph on Cucumber Downy Mildew

TABLE 2

Analysis of results of test of toxicity of benziothiazolinone, dimethomorph and compound benziothiazolinone and dimethomorph on cucumber downy mildew

| Names of reagents | EC$_{50}$ (μg/ml) | ATI | TTI | Co-toxicity coefficient (CTC) |
|---|---|---|---|---|
| Benziothiazolinone | 4.08 | 100.0 | / | / |
| Dimethomorph | 6.36 | 63.9 | / | / |
| Benziothiazolinone:dimethomorph ratio = 50:1 | 2.99 | 136.5 | 99.29 | 137.48 |
| Benziothiazolinone:dimethomorph ratio = 30:1 | 2.40 | 170.0 | 98.835 | 172.00 |
| Benziothiazolinone:dimethomorph ratio = 10:1 | 2.12 | 192.4 | 96.718 | 198.93 |
| Benziothiazolinone:dimethomorph ratio = 1:1 | 2.01 | 203.0 | 81.95 | 247.71 |
| Benziothiazolinone:dimethomorph ratio = 1:10 | 2.91 | 140.2 | 67.18 | 208.69 |
| Benziothiazolinone:dimethomorph ratio = 1:30 | 3.33 | 122.5 | 65.17 | 187.97 |
| Benziothiazolinone:dimethomorph ratio = 1:50 | 4.87 | 83.8 | 64.6 | 129.72 |

The results (Table 2) show that, the compound benziothiazolinone and dimethomorph has significantly improved prevention and treatment effect on cucumber downy mildew, indicating that the compound of the two has a significant synergistic effect on cucumber downy mildew pathogenic fungi. Especially when the ratio of benziothiazolinone and dimethomorph is in the range of 1:30 to 30:1, the co-toxicity coefficient of benziothiazolinone and dithianon is 170 and more, and the synergistic effect is significant.

3. Test of Toxicity of Compound Benziothiazolinone and Iprodione on Cucumber Downy Mildew

TABLE 3

Analysis of results of test of toxicity of benziothiazolinone, iprodione and compound benziothiazolinone and iprodione on cucumber downy mildew

| Names of reagents | $EC_{50}$ (μg/ml) | ATI | TTI | Co-toxicity coefficient (CTC) |
|---|---|---|---|---|
| Benziothiazolinone | 4.21 | 100.00 | / | / |
| Iprodione | 5.82 | 72.34 | / | / |
| Benziothiazolinone:dimethomorph ratio = 50:1 | 3.32 | 126.81 | 99.458 | 127.50 |
| Benziothiazolinone:iprodione ratio = 30:1 | 3.05 | 138.03 | 99.108 | 139.27 |
| Benziothiazolinone:iprodione ratio = 10:1 | 2.29 | 183.84 | 97.485 | 188.58 |
| Benziothiazolinone:iprodione ratio = 1:1 | 2.07 | 203.38 | 86.170 | 236.02 |
| Benziothiazolinone:iprodione ratio = 1:10 | 2.54 | 165.75 | 74.855 | 221.43 |
| Benziothiazolinone:iprodione ratio = 1:30 | 4.18 | 100.72 | 73.232 | 137.54 |
| Benziothiazolinone:iprodione ratio = 1:50 | 4.62 | 91.13 | 72.882 | 125.04 |

The results (Table 3) show that, the compound benziothiazolinone and iprodione has significantly improved prevention and treatment effect on cucumber downy mildew, indicating that the compound of the two has a significant synergistic effect on cucumber downy mildew pathogenic fungi. Especially when the ratio of benziothiazolinone and iprodione is in the range of 1:30 to 30:1, the co-toxicity coefficient of benziothiazolinone and iprodione is 135 and more, and the synergistic effect is significant.

4. Test of Toxicity of Compound Benziothiazolinone and Epoxiconazol on Cucumber Downy Mildew

TABLE 4

Analysis of results of test of toxicity of benziothiazolinone, epoxiconazol and compound benziothiazolinone and epoxiconazol on cucumber downy mildew

| Names of reagents | $EC_{50}$ (μg/ml) | ATI | TTI | Co-toxicity coefficient (CTC) |
|---|---|---|---|---|
| Benziothiazolinone | 3.81 | 100.00 | / | / |
| Epoxiconazol | 4.25 | 89.65 | / | / |
| Benziothiazolinone:Epoxiconazol ratio = 50:1 | 2.90 | 131.343 | 99.797 | 131.61 |
| Benziothiazolinone:epoxiconazol ratio = 30:1 | 2.56 | 148.722 | 99.666 | 149.22 |
| Benziothiazolinone:epoxiconazol ratio = 10:1 | 1.97 | 193.680 | 99.059 | 195.52 |
| Benziothiazolinone:epoxiconazol ratio = 1:1 | 1.59 | 240.106 | 94.825 | 253.21 |
| Benziothiazolinone:epoxiconazol ratio = 1:10 | 1.94 | 196.383 | 90.591 | 216.78 |
| Benziothiazolinone:epoxiconazol ratio = 1:30 | 3.02 | 126.274 | 89.645 | 140.86 |
| Benziothiazolinone:epoxiconazol ratio = 1:50 | 3.51 | 108.403 | 89.353 | 121.32 |

The results (Table 4) show that, the compound benziothiazolinone and epoxiconazol has significantly improved prevention and treatment effect on cucumber downy mildew, indicating that the compound of the two has a significant synergistic effect on cucumber downy mildew pathogenic fungi. Especially when the ratio of benziothiazolinone and epoxiconazol is in the range of 1:30 to 30:1, the co-toxicity coefficient of benziothiazolinone and epoxiconazol is 140 and more, and the synergistic effect is significant.

(II) Field Efficacy Verification Test

Test method: In the early period, the reagent was immediately sprayed for the first time, and 7 days later, the reagent was applied for the second time, each treatment had 4 sections, and each section had a size of 20 m². The incidence was investigated before application of the reagent and 10 days after the second application of the reagent, each section was randomly sampled at 5 points, 5 crops were investigated at each point, the percentage of the lesion area in the leaf area of each leave on the whole crop was investigated, the leaves were graded, and the disease index and the prevention and treatment effect were calculated.

$$\text{Disease index} = \frac{\Sigma(\text{Incidence of leaves of various levels} \times \text{Representative value of this level})}{\text{The total number of leaves} \times \text{Representative value of the highest level}} \times 100$$

$$\text{Prevention and treatment effect } (\%) = \left(1 - \frac{\text{Pre-reagent control disease index} \times \text{Post-reagent treatment disease index}}{\text{Post-reagent control disease index Pre-reagent treatment disease index}}\right) \times 100$$

Expected control efficiency(%)=$X+Y-XY/100$ (where $X$ and $Y$ are control efficiency of single reagent)

Grading Standard:

0 grade: Having no lesion;

1 grade: having less than 5 leaf lesions, and the length of lesions being less than 1 cm;

3 grade: having 6 to 10 leaf lesions, and the length of some lesions being greater than 1 cm;

5 grade: having 11 to 25 leaf lesions, some lesions being contiguous, and the area of the lesions being 10% to 25% of the leaf area;

7 grade: having 26 and more leaf lesions, lesions being contiguous, and the area of the lesions being 26% to 50% of the leaf area;

9 grade: lesions being contiguous, and the area of the lesions being 50% and more of the leaf area or the entire leave withering up.

(1) Field Efficacy Verification Test of Compound Benziothiazolinone and Dithianon on Grape Downy Mildew

TABLE 5

Prevention and treatment effect of compound benziothiazolinone and dithianon mixture on grape downy mildew

| Serial number | Chemicals for treatment | Application amount (a.i.g/ha) | Disease index before application of reagents | 11 days after second application of chemicals — Disease index | Control efficiency (%) |
|---|---|---|---|---|---|
| Embodiment 1 | 15% benziothiazolinone emulsion in water | 125.8 | 2.79 | 6.46 | 85.8 |
| | 50% dithianon suspension | 4.2 | 3.21 | 50.51 | 3.5 |
| | Expected control efficiency after mixing the two components | — | — | — | 86.3 |
| | 62% benziothiazolinone•dithianon water dispersible granule (benziothiazolinone:dithianon = 60:2) | 130.0 | 3.02 | 3.05 | 93.8 |
| Embodiment 2 | 15% benziothiazolinone emulsion in water | 4 | 2.81 | 40.00 | 12.7 |
| | 50% dithianon suspension | 126 | 2.9 | 11.25 | 76.2 |
| | Expected control efficiency after mixing the two components | — | — | — | 79.2 |
| | 65% benziothiazolinone•dithianon water dispersible granule (benziothiazolinone:dithianon = 2:63) | 130.0 | 2.88 | 4.60 | 90.2 |
| Embodiment 9 | 15% benziothiazolinone emulsion in water | 92.8 | 2.69 | 10.75 | 75.5 |
| | 50% dithianon suspension | 37.2 | 2.79 | 39.26 | 13.7 |
| | Expected control efficiency after mixing the two components | — | — | — | 78.9 |
| | 35% benziothiazolinone•dithianon suspension (benziothiazolinone:dithianon = 25:10) | 130.0 | 2.72 | 2.35 | 94.7 |
| Embodiment 10 | 15% benziothiazolinone emulsion in water | 43.4 | 2.85 | 23.56 | 49.3 |
| | 50% dithianon suspension | 86.6 | 2.98 | 30.37 | 37.5 |
| | Expected control efficiency after mixing the two components | — | — | — | 68.3 |
| | 36% benziothiazolinone•dithianon suspension (benziothiazolinone:dithianon = 12:24) | 130.0 | 2.83 | 2.17 | 95.3 |
| Embodiment 17 | 15% benziothiazolinone emulsion in water | 2.9 | 2.76 | 40.87 | 9.2 |
| | 50% dithianon suspension | 127.1 | 3.04 | 11.15 | 77.5 |
| | Expected control efficiency after mixing the two components | — | — | — | 79.6 |
| | 90% benziothiazolinone•dithianon wettable powder (benziothiazolinone:dithianon = 2:88) | 130.0 | 2.93 | 5.83 | 87.8 |
| Embodiment 18 | 15% benziothiazolinone emulsion in water | 127 | 3 | 6.75 | 86.2 |
| | 50% dithianon suspension | 3 | 2.87 | 45.35 | 3.1 |
| | Expected control efficiency after mixing the two components | — | — | — | 86.6 |
| | 88% benziothiazolinone•dithianon wettable powder (benziothiazolinone:dithianon = 86:2) | 130.0 | 2.91 | 4.65 | 90.2 |
| Embodiment 19 | 15% benziothiazolinone emulsion in water | 59 | 2.79 | 20.15 | 55.7 |
| | 50% dithianon suspension | 71 | 2.85 | 31.46 | 32.3 |
| | Expected control efficiency after mixing the two components | — | — | — | 70.0 |
| | 55% benziothiazolinone•dithianon wettable powder (benziothiazolinone:dithianon = 25:30) | 130.0 | 3.02 | 4.19 | 91.5 |
| Embodiment 29 | 15% benziothiazolinone emulsion in water | 21.6 | 2.68 | 28.63 | 34.5 |
| | 50% dithianon suspension | 108.4 | 2.89 | 22.01 | 53.3 |
| | Expected control efficiency after mixing the two components | — | — | — | 69.4 |
| | 18% benziothiazolinone•dithianon microemulsion (benziothiazolinone:dithianon = 3:15) | 130.0 | 2.75 | 3.36 | 92.5 |
| Embodiment 30 | 15% benziothiazolinone emulsion in water | 108.4 | 2.87 | 10.06 | 78.5 |
| | 50% dithianon suspension | 21.6 | 2.93 | 43.62 | 8.7 |
| | Expected control efficiency after mixing the two components | — | — | — | 80.37 |
| | 30% benziothiazolinone•dithianon microemulsion (benziothiazolinone:dithianon = 25:5) | 130.0 | 2.85 | 3.63 | 92.2 |
| Embodiment 37 | 15% benziothiazolinone emulsion in water | 123.8 | 2.68 | 6.86 | 84.3 |
| | 50% dithianon suspension | 6.2 | 2.89 | 45.15 | 4.2 |
| | Expected control efficiency after mixing the | — | — | — | 84.96 |

TABLE 5-continued

Prevention and treatment effect of compound benziothiazolinone and dithianon mixture on grape downy mildew

| Serial number | Chemicals for treatment | Application amount (a.i.g/ha) | Disease index before application of reagents | 11 days after second application of chemicals | |
|---|---|---|---|---|---|
| | | | | Disease index | Control efficiency (%) |
| | two components | | | | |
| | 42% benziothiazolinone•dithianon microemulsion (benziothiazolinone:dithianon = 40:2) | 130.0 | 2.75 | 3.86 | 91.4 |
| Embodiment 38 | 15% benziothiazolinone emulsion in water | 11.8 | 2.76 | 34.34 | 23.7 |
| | 50% dithianon suspension | 118.2 | 2.85 | 16.03 | 65.5 |
| | Expected control efficiency after mixing the two components | — | — | — | 73.7 |
| | 44% benziothiazolinone•dithianon microemulsion (benziothiazolinone:dithianon == 4:40) | 130.0 | 3.11 | 3.14 | 93.8 |
| Embodiment 45 | 15% benziothiazolinone emulsion in water | 6.2 | 2.9 | 39.11 | 17.3 |
| | 50% dithianon suspension | 123.8 | 2.85 | 14.36 | 69.1 |
| | Expected control efficiency after mixing the two components | — | — | — | 74.4 |
| | 42% benziothiazolinone•dithianon microemulsion (benziothiazolinone:dithianon = 2:40) | 130 | 2.79 | 4.32 | 90.5 |
| Embodiment 46 | 15% benziothiazolinone emulsion in water | 118.2 | 3.05 | 9.05 | 81.8 |
| | 50% dithianon suspension | 11.8 | 3.25 | 49.23 | 7.1 |
| | Expected control efficiency after mixing the two components | — | — | — | 83.1 |
| | 55% benziothiazolinone•dithianon microemulsion (benziothiazolinone:dithianon = 50:5) | 130 | 2.99 | 3.17 | 93.5 |
| Water control (CK) | — | — | 2.93 | 46.93 | — |

Test results (Table 5) show that, the compound benziothiazolinone and dithianon has significantly improved control efficiency on grape downy mildew, indicating that the compound of the two has a significant synergistic effect on grape downy mildew.

(2) Field Efficacy Verification Test of Compound Benziothiazolinone and Dimethomorph on Litchi Blight

TABLE 6

Prevention and treatment effect of compound benziothiazolinone and dimethomorph on litchi blight

| Serial number | Chemicals for treatment | Application amount (a.i.g/ha) | Disease index before application of reagents | 11 days after second application of chemicals | |
|---|---|---|---|---|---|
| | | | | Disease index | Control efficiency (%) |
| Embodiment 3 | 15% benziothiazolinone emulsion in water | 145.4 | 2.51 | 5.95 | 81.2 |
| | 50% dimethomorph wettable powder | 19.6 | 2.63 | 30.89 | 6.8 |
| | Expected control efficiency after mixing the two components | — | — | — | 82.5 |
| | 65% benziothiazolinone•dimethomorph water dispersible granule (benziothiazolinone:dimethomorph = 63:2) | 150.0 | 2.52 | 3.52 | 88.9 |
| Embodiment 4 | 15% benziothiazolinone emulsion in water | 3.5 | 2.32 | 28.50 | 2.5 |
| | 50% dimethomorph wettable powder | 146.5 | 2.29 | 6.95 | 75.9 |
| | Expected control efficiency after mixing the two components | — | — | — | 76.5 |
| | 85% benziothiazolinone•dimethomorph water dispersible granule (benziothiazolinone:dimethomorph = 2:83) | 150 | 2.52 | 4.51 | 85.8 |

TABLE 6-continued

Prevention and treatment effect of compound benziothiazolinone and dimethomorph on litchi blight

| Serial number | Chemicals for treatment | Application amount (a.i.g/ha) | Disease index before application of reagents | 11 days after second application of chemicals Disease index | Control efficiency (%) |
|---|---|---|---|---|---|
| Embodiment 11 | 15% benziothiazolinone emulsion in water | 142.9 | 2.45 | 6.14 | 80.1 |
| | 50% dimethomorph wettable powder | 7.1 | 2.38 | 28.40 | 5.3 |
| | Expected control efficiency after mixing the two components | — | — | — | 81.2 |
| | 42% benziothiazolinone•dimethomorph suspension (benziothiazolinone:dimethomorph = 40:2) | 150.0 | 2.53 | 4.50 | 85.9 |
| Embodiment 12 | 15% benziothiazolinone emulsion in water | 23.4 | 2.26 | 21.47 | 24.6 |
| | 50% dimethomorph wettable powder | 126.6 | 2.64 | 12.81 | 61.5 |
| | Expected control efficiency after mixing the two components | — | — | — | 71.0 |
| | 32% benziothiazolinone•dimethomorph suspension (benziothiazolinone:dimethomorph = 5:27) | 150 | 2.65 | 4.37 | 86.9 |
| Embodiment 20 | 15% benziothiazolinone emulsion in water | 146.6 | 2.54 | 5.60 | 82.5 |
| | 50% dimethomorph wettable powder | 3.4 | 2.52 | 30.90 | 2.7 |
| | Expected control efficiency after mixing the two components | — | — | — | 83.0 |
| | 88% benziothiazolinone•dimethomorph wettable powder (benziothiazolinone:dimethomorph = 86:2) | 150.0 | 2.51 | 4.36 | 86.2 |
| Embodiment 21 | 15% benziothiazolinone emulsion in water | 75.0 | 2.72 | 14.29 | 58.3 |
| | 50% dimethomorph wettable powder | 75.0 | 2.81 | 23.79 | 32.8 |
| | Expected control efficiency after mixing the two components | — | — | — | 72.0 |
| | benziothiazolinone•dimethomorph wettable powder (benziothiazolinone:dimethomorph = 25:25) | 150.0 | 2.41 | 3.49 | 88.5 |
| Embodiment 22 | 15% benziothiazolinone emulsion in water | 4.8 | 2.36 | 28.58 | 3.9 |
| | 50% dimethomorph wettable powder | 145.2 | 2.32 | 7.54 | 74.2 |
| | Expected control efficiency after mixing the two components | — | — | — | 75.2 |
| | 50% benziothiazolinone•dimethomorph wettable powder (benziothiazolinone:dimethomorph = 2:60) | 150.0 | 2.55 | 4.88 | 84.8 |
| Embodiment 31: | 15% benziothiazolinone emulsion in water | 50.0 | 2.82 | 21.07 | 40.7 |
| | 50% dimethomorph wettable powder | 100.0 | 2.53 | 16.74 | 47.5 |
| | Expected control efficiency after mixing the two components | — | — | — | 68.9 |
| | 15% benziothiazolinone•dimethomorph microemulsion (benziothiazolinone:dimethomorph = 5:10) | 150.0 | 2.63 | 3.48 | 89.5 |
| Embodiment 32 | 15% benziothiazolinone emulsion in water | 100.0 | 2.66 | 10.66 | 68.2 |
| | 50% dimethomorph wettable powder | 50.0 | 2.39 | 22.86 | 24.1 |
| | Expected control efficiency after mixing the two components | — | — | — | 75.9 |
| | 15% benziothiazolinone•dimethomorph microemulsion (benziothiazolinone:dimethomorph == 10:5) | 150.0 | 2.35 | 3.58 | 87.9 |
| Embodiment 39 | 15% benziothiazolinone emulsion in water | 136.4 | 2.56 | 6.90 | 78.6 |
| | 50% dimethomorph wettable powder | 13.6 | 2.25 | 26.91 | 5.1 |
| | Expected control efficiency after mixing the two components | — | — | — | 79.7 |
| | 22% benziothiazolinone•dimethomorph emulsion in water (benziothiazolinone:dimethomorph = 20:2) | 150.0 | 3.01 | 5.20 | 86.3 |
| Embodiment 40 | 15% benziothiazolinone emulsion in water | 13.6 | 2.51 | 27.14 | 14.2 |
| | 50% dimethomorph wettable powder | 136.4 | 2.62 | 10.63 | 67.8 |
| | Expected control efficiency after mixing the two components | — | — | — | 72.4 |
| | 22% benziothiazolinone•dimethomorph emulsion in water (benziothiazolinone:dimethomorph = 2:20) | 150.0 | 2.51 | 3.83 | 87.9 |
| Embodiment 47 | 15% benziothiazolinone emulsion in water | 125.0 | 2.52 | 8.35 | 73.7 |
| | 50% dimethomorph wettable powder | 25.0 | 2.35 | 26.77 | 9.6 |
| | Expected control efficiency after mixing the two components | — | — | — | 76.2 |

TABLE 6-continued

Prevention and treatment effect of compound benziothiazolinone and dimethomorph on litchi blight

| Serial number | Chemicals for treatment | Application amount (a.i.g/ha) | Disease index before application of reagents | 11 days after second application of chemicals | |
|---|---|---|---|---|---|
| | | | | Disease index | Control efficiency (%) |
| | 30% benziothiazolinone•dimethomorph oil suspension (benziothiazolinone:dimethomorph = 25:5) | 150.0 | 2.69 | 4.91 | 85.5 |
| Embodiment 48 | 15% benziothiazolinone emulsion in water | 7.1 | 2.55 | 29.95 | 6.8 |
| | 50% dimethomorph wettable powder | 142.9 | 2.21 | 8.02 | 71.2 |
| | Expected control efficiency after mixing the two components | — | — | — | 73.2 |
| | 42% benziothiazolinone•dimethomorph oil suspension (benziothiazolinone:dimethomorph = 2:40) | 150.0 | 2.36 | 4.10 | 86.2 |
| Water control (CK) | — | — | 2.58 | 32.51 | — |

Test results (Table 6) show that, the compound benziothiazolinone and dimethomorph has significantly improved control efficiency on litchi blight, indicating that the compound of the two has a significant synergistic effect on litchi blight.

(3) Field Efficacy Verification Test of Compound Benziothiazolinone and Iprodione on Pepper Cinerea

TABLE 7

Prevention and treatment effect of compound benziothiazolinone and iprodione on pepper cinerea

| Serial number | Chemicals for treatment | Application amount (a.i.g/ha) | Disease index before application of reagents | 11 days after second application of chemicals | |
|---|---|---|---|---|---|
| | | | | Disease index | Control efficiency (%) |
| Embodiment 5 | 15% benziothiazolinone emulsion in water | 174.2 | 3.32 | 9.60 | 75.8 |
| | 50% iprodione suspension | 5.8 | 3.11 | 35.98 | 3.2 |
| | Expected control efficiency after mixing the two components | — | — | — | 76.6 |
| | 62% benziothiazolinone•iprodione water dispersible granule (benziothiazolinone:iprodione = 60:2) | 180.0 | 3.52 | 6.77 | 83.9 |
| Embodiment 6 | 15% benziothiazolinone emulsion in water | 4.8 | 3.32 | 35.91 | 9.5 |
| | 50% iprodione suspension | 175.2 | 3.89 | 14.09 | 69.7 |
| | Expected control efficiency after mixing the two components | — | — | — | 72.6 |
| | 75% benziothiazolinone•iprodione water dispersible granule (benziothiazolinone:iprodione = 2:73) | 180.0 | 3.51 | 7.26 | 82.7 |
| Embodiment 13 | 15% benziothiazolinone emulsion in water | 163.6 | 2.85 | 10.01 | 70.6 |
| | 50% iprodione suspension | 16.4 | 2.98 | 32.30 | 9.3 |
| | Expected control efficiency after mixing the two components | — | — | — | 73.3 |
| | 55% benziothiazolinone•iprodione suspension (benziothiazolinone:iprodione = 50:5) | 180.0 | 3.11 | 5.91 | 84.1 |
| Embodiment 14 | 15% benziothiazolinone emulsion in water | 8.6 | 3.21 | 32.30 | 15.8 |
| | 50% iprodione suspension | 171.4 | 3.14 | 13.81 | 63.2 |
| | Expected control efficiency after mixing the two components | — | — | — | 69.0 |
| | 42% benziothiazolinone•iprodione suspension (benziothiazolinone:iprodione = 2:40) | 180.0 | 3.15 | 6.55 | 82.6 |
| Embodiment 23 | 15% benziothiazolinone emulsion in water | 175.8 | 2.84 | 8.11 | 76.1 |
| | 50% iprodione suspension | 4.2 | 2.92 | 33.88 | 2.9 |
| | Expected control efficiency after mixing the two components | — | — | — | 76.8 |

TABLE 7-continued

Prevention and treatment effect of compound benziothiazolinone and iprodione on pepper cinerea

| Serial number | Chemicals for treatment | Application amount (a.i.g/ha) | Disease index before application of reagents | 11 days after second application of chemicals | |
|---|---|---|---|---|---|
| | | | | Disease index | Control efficiency (%) |
| | 85% benziothiazolinone•iprodione wettable powder (benziothiazolinone:iprodione = 83:2) | 180.0 | 2.82 | 5.59 | 83.4 |
| Embodiment 24 | 15% benziothiazolinone emulsion in water | 90.0 | 3.76 | 23.68 | 47.3 |
| | 50% iprodione suspension | 90.0 | 3.24 | 26.60 | 31.3 |
| | Expected control efficiency after mixing the two components | — | — | — | 63.8 |
| | 50% benziothiazolinone•iprodione wettable powder (benziothiazolinone:iprodione = 25:25) | 180.0 | 3.35 | 4.88 | 87.8 |
| Embodiment 25 | 15% benziothiazolinone emulsion in water | 4.2 | 3.31 | 35.68 | 9.8 |
| | 50% iprodione suspension | 175.8 | 3.22 | 13.70 | 64.4 |
| | Expected control efficiency after mixing the two components | — | — | — | 67.9 |
| | 85% benziothiazolinone•iprodione wettable powder (benziothiazolinone:iprodione = 2:83) | 180.0 | 3.45 | 7.38 | 82.1 |
| Embodiment 33 | 15% benziothiazolinone emulsion in water | 60.0 | 3.72 | 30.90 | 30.5 |
| | 50% iprodione suspension | 120.0 | 3.13 | 18.25 | 51.2 |
| | Expected control efficiency after mixing the two components | — | — | — | 66.1 |
| | 18% benziothiazolinone•iprodione microemulsion (benziothiazolinone:iprodione = 6:12) | 180.0 | 3.42 | 4.82 | 88.2 |
| Embodiment 34 | 15% benziothiazolinone emulsion in water | 171.4 | 3.26 | 10.05 | 74.2 |
| | 50% iprodione suspension | 8.6 | 3.11 | 35.20 | 5.3 |
| | Expected control efficiency after mixing the two components | — | — | — | 75.6 |
| | 21% benziothiazolinone•iprodione microemulsion (benziothiazolinone:iprodione = 20:1) | 180.0 | 3.32 | 6.55 | 83.5 |
| Embodiment 41 | 15% benziothiazolinone emulsion in water | 150.0 | 3.56 | 15.91 | 62.6 |
| | 50% iprodione suspension | 30.0 | 3.25 | 31.19 | 19.7 |
| | Expected control efficiency after mixing the two components | — | — | — | 70.0 |
| | 30% benziothiazolinone•iprodione emulsion in water (benziothiazolinone:iprodione = 25:5) | 180.0 | 3.41 | 5.34 | 86.9 |
| Embodiment 42 | 15% benziothiazolinone emulsion in water | 8.6 | 3.51 | 35.44 | 15.5 |
| | 50% iprodione suspension | 171.4 | 3.12 | 14.43 | 61.3 |
| | Expected control efficiency after mixing the two components | — | — | — | 67.3 |
| | 42% benziothiazolinone•iprodione emulsion in water (benziothiazolinone:iprodione = 2:40) | 180.0 | 3.11 | 6.28 | 83.1 |
| Embodiment 49 | 15% benziothiazolinone emulsion in water | 30.0 | 3.22 | 30.48 | 20.8 |
| | 50% iprodione suspension | 150.0 | 2.96 | 13.69 | 61.3 |
| | Expected control efficiency after mixing the two components | — | — | — | 69.3 |
| | 18% benziothiazolinone•iprodione oil suspension (benziothiazolinone:iprodione = 3:15) | 180.0 | 2.90 | 3.99 | 88.5 |
| Embodiment 50 | 15% benziothiazolinone emulsion in water | 163.6 | 2.86 | 10.36 | 69.7 |
| | 50% iprodione suspension | 16.4 | 2.91 | 31.44 | 9.6 |
| | Expected control efficiency after mixing the two components | — | — | — | 72.6 |
| | 22% benziothiazolinone•iprodione oil suspension (benziothiazolinone:iprodione = 20:2) | 180.0 | 3.19 | 6.33 | 83.4 |
| Water control (CK) | — | — | 3.21 | 38.36 | — |

Test results (Table 7) show that, the compound benziothiazolinone and iprodione has significantly improved control efficiency on pepper cinerea, indicating that the compound of the two has a significant synergistic effect on pepper cinerea.

(4) Field Efficacy Verification Test of Compound Benziothiazolinone and Epoxiconazol Mixture on Sigatoka

TABLE 8

Prevention and treatment effect of compound benziothiazolinone and epoxiconazol on sigatoka

| Serial number | Chemicals for treatment | Application amount (a.i.g/ha) | Disease index before application of reagents | 11 days after second application of chemicals | |
|---|---|---|---|---|---|
| | | | | Disease index | Control efficiency (%) |
| Embodiment 7 | 15% benziothiazolinone emulsion in water | 96.8 | 3.11 | 9.90 | 76.2 |
| | 50% epoxiconazol suspension | 3.2 | 3.23 | 41.45 | 4.1 |
| | Expected control efficiency after mixing the two components | — | — | — | 77.2 |
| | 62% benziothiazolinone•epoxiconazol water dispersible granule (benziothiazolinone:epoxiconazol ratio = 60:2) | 100.0 | 3.52 | 7.49 | 84.1 |
| Embodiment 8 | 15% benziothiazolinone emulsion in water | 3.2 | 3.81 | 47.26 | 7.3 |
| | 50% epoxiconazol suspension | 96.8 | 3.92 | 17.41 | 66.8 |
| | Expected control efficiency after mixing the two components | — | — | — | 69.2 |
| | 62% benziothiazolinone•epoxiconazol water dispersible granule (benziothiazolinone:epoxiconazol ratio = 2:60) | 100.0 | 3.28 | 7.55 | 82.8 |
| Embodiment 15 | 15% benziothiazolinone emulsion in water | 90.9 | 3.69 | 13.77 | 72.1 |
| | 50% epoxiconazol suspension | 9.1 | 3.72 | 46.44 | 6.7 |
| | Expected control efficiency after mixing the two components | — | — | — | 74.0 |
| | 55% benziothiazolinone•epoxiconazol suspension (benziothiazolinone:epoxiconazol ratio = 50:5) | 100.0 | 3.71 | 7.10 | 85.7 |
| Embodiment 16 | 15% benziothiazolinone emulsion in water | 9.1 | 3.55 | 38.52 | 18.9 |
| | 50% epoxiconazol suspension | 90.9 | 3.88 | 20.40 | 60.7 |
| | Expected control efficiency after mixing the two components | — | — | — | 68.1 |
| | 55% benziothiazolinone•epoxiconazol suspension (benziothiazolinone:epoxiconazol ratio = 5:50) | 100.0 | 3.83 | 7.28 | 85.8 |
| Embodiment 26 | 15% benziothiazolinone emulsion in water | 2.3 | 3.56 | 44.82 | 5.9 |
| | 50% epoxiconazol suspension | 97.7 | 3.34 | 14.39 | 67.8 |
| | Expected control efficiency after mixing the two components | — | — | — | 69.7 |
| | 88% benziothiazolinone•epoxiconazolwettable powder (benziothiazolinone:epoxiconazol ratio = 2:86) | 100.0 | 3.63 | 8.21 | 83.1 |
| Embodiment 27 | 15% benziothiazolinone emulsion in water | 97.3 | 3.55 | 11.16 | 76.5 |
| | 50% epoxiconazol suspension | 2.3 | 3.87 | 49.76 | 3.9 |
| | Expected control efficiency after mixing the two components | — | — | — | 77.4 |
| | 86% benziothiazolinone•epoxiconazol wettable powder (benziothiazolinone:epoxiconazol ratio = 84:2) | 100.0 | 3.93 | 9.04 | 82.8 |
| Embodiment 28 | 15% benziothiazolinone emulsion in water | 50.0 | 3.59 | 25.22 | 47.5 |
| | 50% epoxiconazol suspension | 50.0 | 3.55 | 30.97 | 34.8 |
| | Expected control efficiency after mixing the two components | — | — | — | 65.8 |
| | 50% benziothiazolinone•epoxiconazol wettable powder (benziothiazolinone:epoxiconazol ratio = 25:25) | 100.0 | 3.42 | 6.96 | 84.8 |
| Embodiment 35 | 15% benziothiazolinone emulsion in water | 16.7 | 3.83 | 37.00 | 27.8 |
| | 50% epoxiconazol suspension | 83.3 | 3.89 | 24.72 | 52.5 |
| | Expected control efficiency after mixing the two components | — | — | — | 65.7 |
| | 12% benziothiazolinone•epoxiconazol microemulsion (benziothiazolinone:epoxiconazol ratio = 2:10) | 100.0 | 3.65 | 6.40 | 86.9 |
| Embodiment 36 | 15% benziothiazolinone emulsion in water | 66.7 | 3.87 | 25.73 | 50.3 |
| | 50% epoxiconazol suspension | 33.3 | 3.93 | 41.28 | 21.5 |
| | Expected control efficiency after mixing the two components | — | — | — | 61.0 |
| | 15% benziothiazolinone•epoxiconazol microemulsion (benziothiazolinone:epoxiconazol ratio = 10:5) | 100.0 | 365 | 800.92 | 83.6 |

TABLE 8-continued

Prevention and treatment effect of compound benziothiazolinone and epoxiconazol on sigatoka

| Serial number | Chemicals for treatment | Application amount (a.i.g/ha) | Disease index before application of reagents | 11 days after second application of chemicals | |
|---|---|---|---|---|---|
| | | | | Disease index | Control efficiency (%) |
| Embodiment 43 | 15% benziothiazolinone emulsion in water | 95.2 | 3.68 | 12.41 | 74.8 |
| | 50% epoxiconazol suspension | 4.8 | 3.89 | 49.34 | 5.2 |
| | Expected control efficiency after mixing the two components | — | — | — | 76.1 |
| | 21% benziothiazolinone•epoxiconazol emulsion in water (benziothiazolinone:epoxiconazol ratio = 20:1) | 100.0 | 2.75 | 5.78 | 84.3 |
| Embodiment 44 | 15% benziothiazolinone emulsion in water | 4.8 | 3.76 | 45.38 | 9.8 |
| | 50% epoxiconazol suspension | 95.2 | 3.55 | 15.86 | 66.6 |
| | Expected control efficiency after mixing the two components | — | — | — | 69.9 |
| | 42% benziothiazolinone•epoxiconazol emulsion in water (benziothiazolinone:epoxiconazol ratio = 2:40) | 100.0 | 3.31 | 6.60 | 85.1 |
| Embodiment 51 | 15% benziothiazolinone emulsion in water | 83.3 | 3.69 | 18.51 | 62.5 |
| | 50% epoxiconazol suspension | 16.7 | 3.82 | 43.29 | 15.3 |
| | Expected control efficiency after mixing the two components | — | — | — | 68.2 |
| | 30% benziothiazolinone•epoxiconazol oil suspension (benziothiazolinone:epoxiconazol ratio = 25:5) | 100.0 | 3.79 | 7.51 | 85.2 |
| Embodiment 52 | 15% benziothiazolinone emulsion in water | 33.3 | 3.55 | 31.78 | 33.1 |
| | 50% epoxiconazol suspension | 66.7 | 3.65 | 29.20 | 40.2 |
| | Expected control efficiency after mixing the two components | — | — | — | 60.0 |
| | 45% benziothiazolinone•epoxiconazol oil suspension (benziothiazolinone:epoxiconazol ratio = 15:30) | 100.0 | 3.49 | 6.44 | 86.2 |
| Water control (CK) | — | — | 3.58 | 47.9 | — |

Test results (Table 8) show that, the compound benziothiazolinone and epoxiconazol has significantly improved control efficiency on sigatoka, indicating that the compound of the two has a significant synergistic effect on sigatoka.

What is claimed is:

1. A synergistic fungicide composition, comprising two active components A and B, wherein the active component A is benziothiazolinone, the active component B is one selected from the group consisting of dithianon, dimethomorph, iprodione and epoxiconazol, and the weight ratio of the two components is 1:50 to 50:1.

2. The composition according to claim 1, wherein the composition is composed of 6 wt % to 92 wt % of the active components and 94 wt % to 8 wt % of fungicide adjuvants.

3. The composition according to claim 1, wherein the weight ratio of the active component benziothiazolinone and the active component dithianon is 1:30 to 30:1.

4. The composition according to claim 1, wherein the weight ratio of the active component benziothiazolinone and the active component dimethomorph is 1:30 to 30:1.

5. The composition according to claim 1, wherein the weight ratio of the active component benziothiazolinone and the active component iprodione is 1:30 to 30:1.

6. The composition according to claim 1, wherein the weight ratio of the active component benziothiazolinone and the active component epoxiconazol is 1:30 to 30:1.

7. The composition according to claim 1, wherein the composition is formulated into any formulation allowable in agriculture.

8. The composition according to claim 5, wherein the composition is formulated into wettable powder, a suspension, an oil suspension, a water dispersible granule, an emulsion in water and a microemulsion.

* * * * *